(12) United States Patent
Gnutzmann et al.

(10) Patent No.: US 8,253,121 B2
(45) Date of Patent: Aug. 28, 2012

(54) METHOD FOR CREATING A THERAPY PLAN

(75) Inventors: Tobias Gnutzmann, Nürnberg (DE); Tim Use, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 105 days.

(21) Appl. No.: 12/775,152

(22) Filed: May 6, 2010

(65) Prior Publication Data

US 2010/0288945 A1 Nov. 18, 2010

(30) Foreign Application Priority Data

May 13, 2009 (DE) .......................... 10 2009 021 024

(51) Int. Cl.
*A61N 5/10* (2006.01)
*G01J 1/00* (2006.01)

(52) U.S. Cl. .................. 250/503.1; 250/492.3; 378/156; 378/18

(58) Field of Classification Search .............. 250/492.1, 250/492, 21, 492.22, 492.23, 492.3, 503.1; 378/18, 156, 159
See application file for complete search history.

(56) References Cited

U.S. PATENT DOCUMENTS

| | | | | |
|---|---|---|---|---|
| 3,715,587 | A * | 2/1973 | Burkhalter et al. | 378/195 |
| 5,526,394 | A * | 6/1996 | Siczek et al. | 378/37 |
| 6,108,403 | A * | 8/2000 | Cooper et al. | 378/156 |
| 6,816,564 | B2 * | 11/2004 | Charles et al. | 378/5 |
| 6,826,423 | B1 * | 11/2004 | Hardy et al. | 600/429 |
| 2002/0106054 | A1 * | 8/2002 | Caflisch et al. | 378/65 |
| 2004/0210289 | A1 * | 10/2004 | Wang et al. | 607/116 |
| 2008/0123810 | A1 * | 5/2008 | Kirkpatrick et al. | 378/65 |
| 2009/0116616 | A1 | 5/2009 | Lu et al. | |
| 2010/0301228 | A1 * | 12/2010 | Pu | 250/396 R |

FOREIGN PATENT DOCUMENTS

| | | |
|---|---|---|
| DE | 4223488 A1 | 1/1994 |
| DE | 10227808 A1 | 1/2004 |
| DE | 102005038242 B3 | 4/2007 |
| GB | 2068700 A | 8/1981 |
| WO | WO 2005081842 A2 | 9/2005 |
| WO | WO 2008156803 A2 | 12/2008 |

OTHER PUBLICATIONS

European Search Report and Written Opinion dated Jun. 24, 2010 for corresponding European Patent Application No. EP 10 156 902.8 with English translation.
German Office Action dated Jan. 25, 2010 for corresponding German Patent Application No. DE 10 2009 021 024.5 with English translation.
"VYSE Professional Ballistic & Ordnance Gelatin—the clear difference," http://www.gelatininnovations.com/pages/ballistic.html, Dec. 5, 2009.

* cited by examiner

*Primary Examiner* — Bernard E Souw
(74) *Attorney, Agent, or Firm* — Lempia Summerfield Katz LLC

(57) ABSTRACT

A method for creating a therapy plan for a particle therapy, in which a filter is used to adjust the depth of penetration of the particle beam and an immobilization device is used to immobilize a body region of a patient to be treated, includes adjusting the geometry of a deformable mass of a filter to the geometry of the immobilization device. The deformable filter mass is applied, at least partially, to the immobilization device. A planning data record is obtained with recordings of the filter, so that the properties of the filter are determined on the basis of the recordings and are used in the therapy plan.

19 Claims, 1 Drawing Sheet

METHOD FOR CREATING A THERAPY PLAN

This application claims the benefit of DE 10 2009 021 024.5 filed May 13, 2009, which is hereby incorporated by reference.

BACKGROUND

The present embodiments relate to a method for creating a therapy plan for a particle therapy and a filter apparatus for a particle therapy system.

During a particle therapy treatment (e.g., of cancerous diseases), a particle beam made up of protons or heavy ions (e.g., carbon ions) is generated in a suitable accelerator. The particle beam is guided into a treatment room using beam control and enters the treatment room by way of an exit window. The particle beam may alternately be directed into different treatment rooms by an accelerator. In the treatment room, a patient to be treated is positioned on a patient couch, for example, and may be immobilized using an immobilization device.

The irradiation of a target area (e.g., a tumor, tissue) may take place layer by layer. As a function of the energy of the particle beam, the particle beam reaches different depths in the tissue, so that the tissue can be subdivided into disk-type sections or layers of the same depth of penetration. The focused particle beam is moved across the individual layers of the target area (e.g., "beam scanning"), so that several points within a layer, which lie on a grid for example, are irradiated. As the radiation intensity and/or energies are selected correctly, regions with a complicated structure can also be irradiated accurately. The arrangement of the layers and points to be irradiated is selected such that the planned dose distribution can be achieved.

During irradiation with an accelerator, minimal energy, which the accelerator is to provide with respect to a good beam quality, is needed. This minimal energy corresponds to a water equivalent thickness of 20 mm, for example (i.e., the beam reaches 20 mm into the tissue). As a result of the minimal energy required, the active energy modulation of the accelerator enables target areas, which are located at 20 mm or lower below the skin surface, to be treated. To reach the tissue between the skin and 20 mm below the skin surface, a passive filter (e.g., a "range shifter") is provided, which decelerates the particle beam so that the irradiation of tumors close to the skin is enabled. Such a filter is generally made from a water-equivalent material such as, for example, PMMA. The filter, generally made in the manner of a plate, is held between the beam exit and the patient and has an intensity which corresponds to the 20 mm water equivalence, for example. A deceleration of the beam energy within the filter plate therefore takes place, and the irradiation of a body region to be treated immediately behind the filter plate is enabled.

Since scattering effects take place as a result of the interaction between the particle beam and the atoms of the filter plate, the filter plate is positioned as close as possible to the patient. Furthermore, the orthogonality of the filter plate relative to the particle beam must be ensured.

With current accelerators, the filter is usually adjustably arranged in the region of the exit window, and when removing the filter for the therapy, the filter plate often collides with the patient couch.

To treat a patient with the particle beam, a therapy plan is created beforehand. The therapy plan defines which layers of the target area (e.g., the tumor) are to be radiated with which dose and from which direction. The aim is to irradiate the tumor as efficiently as possible, with organs at risk (e.g., an optic nerve or parts of the brain) being excluded from the irradiation or the applied dose in the healthy tissue of the "irradiation channel" being minimized.

With current therapy planning systems, the "range shifter", which is a rigid plate with a constant water-equivalent thickness, is provided in the therapy plan. The real thickness, quality and homogeneity of the plate material are not measured by the planning system. Instead, prior to using the filter plate for the first time, the properties of the filter plate are determined in a complicated process and used as constant variables in subsequent therapies.

SUMMARY AND DESCRIPTION

The present embodiments may obviate one or more of the drawbacks or limitations in the related art. For example, in one embodiment, an improvement in the therapy planning for an irradiation with a particle therapy system is provided.

In one embodiment, a method for creating a therapy plan for a particle therapy, in which a filter is used to set the depth of penetration of the particle beam and an immobilization device is used to immobilize a body region of a patient to be treated, includes adjusting the geometry of a deformable filter mass of the filter to the geometry of the immobilization device, applying, at least partially, the filter to the immobilization device, obtaining a planning data record with a recording of the filter, and determining the properties of the filter to be used for the therapy plan on the basis of the recording.

The method is based on the use of a filter mass, which is applied to the immobilization device and the properties of which are accounted for during the therapy planning, in a particle therapy, so that the treatment is planned very precisely. The filter mass is easily deformable, has a relatively high homogeneity with respect to the water equivalence of the filter mass and has long term stability with respect to the water content of the filter mass (e.g., the material does not dry out during the treatment and does not shrink).

Prior to the treatment, the patient may be immobilized using the immobilization device, and a planning scan of the body region to be treated (e.g., using a computed tomography (CT) device) is obtained. In one embodiment, the recordings are obtained with the CT device if the body region to be treated is positioned in an isocenter of the particle therapy system and is held in this position using the immobilization device. Data relating to the shape, size and/or position of the tumor is obtained in this way and stored in a planning data record. The filter mass applied to the immobilization device is also recorded in the same or in a separate planning scan so that similarly accurate data relating to the filter is available. The data relating to the filter is used in the therapy planning, and the energy and the duration with which the filter is to be irradiated is calculated.

The immobilization device is a mounting and positioning system made of, for example, foam or carbon, which is widely used in beam therapy in order to ensure the proper positioning of the patient with respect to the isocenter of the particle therapy system during the irradiation on different irradiation days. An example of such an immobilization device is an immobilization mask, which is fastened to, for example, a small head plate or a head-shoulder plate, for placing on the face of the patient, so that head movement of the patient is prevented.

By using a filter, which is made from a deformable filter mass and replaces the rigid filter plates, the filter mass may be easily attached close to the patient by directly attaching the filter mass to the immobilization device. The filter is thus decoupled from the accelerator, and a complicated movement mechanism for moving the filter is not needed, so that collisions with the patient couch or the remaining mechanical elements of the accelerator may be avoided. Maintenance of the particle therapy system is simplified since the particle therapy system is no longer coupled to the maintenance of the filter or a movement mechanism of the filter. In particular, prior to treatment, the filter mass is attached to the immobilization device outside of the treatment room. Therefore, the patient's stay in the treatment room is shortened and the treatment program is optimized with respect to a consecutive irradiation of several patients.

The filter mass is also applied individually to the patient in different thicknesses and sizes. In most cases, it is sufficient to cover one subregion of the immobilization device with the filter mass (e.g., only a subregion with a diameter of approximately 15 cm).

As the filter mass is adjusted to the contour of the immobilization device and thus of the patient, the filter is unrestrictedly suited to treatments from different directions.

In one embodiment, the therapy plan is created taking account of the thickness distribution and/or homogeneity of the filter mass. As in the planning data record, precise information relating to the thickness of the filter mass is contained at any point and taken into account during the therapy planning. The requirements in terms of geometry are minimal and small deviations from a desired thickness are permitted. Information relating to the homogeneity of the filter mass in the different regions of the filter is obtained using the planning scan, so that the requirements for homogeneity are likewise reduced during the manufacture of the filter.

In one embodiment, an immobilization mask is used as an immobilization device. The immobilization mask may be made of a thermoplastic mask material, which, at a water temperature of approximately 65°, is brought into a deformable state and adjusted to the corresponding patient contour. The immobilization mask is adjusted to the patient within a planning step, and the filter mass is applied to the immobilization mask.

A mass that hardens after adopting the form of the immobilization device is suitable as a filter mass. In one embodiment, the filter mass remains relatively soft after application so that the filter mass changes shape or position in some circumstances (e.g., under the influence of the weight of the filter mass). In one embodiment, a cover, which is used to fix the filter mass, is applied to the surface of the filter mass. The cover has a much lower strength in comparison with the filter mass (e.g., 1:20), so that the influence of the cover on the energy of the particle beam when penetrating the cover material is minimal. The cover may be made of plastic or the same material as the immobilization device, for example, and have a network-type structure or be configured in the manner of a fixing layer or fixing film.

In one embodiment, a first planning data record is obtained with recordings of the body region to be treated, which is immobilized using the immobilization device. A second planning data record is obtained with recordings of the immobilization device using the filter, and both planning data records are compared with one another to optimize the therapy plan. During a second planning scan, the immobilization device and the filter are detected, without being placed on the patient. This procedure is particularly efficient if data relating to the patient already exists and is only to be elaborated by the information relating to the filter in order to plan the treatment optimally. A planning scan of the patient is implemented with the immobilization device, so that the accurate geometry of the immobilization device is detected during the irradiation. It is after the point at which the particle beam penetrates the immobilization device is known that the filter mass is applied to the immobilization device and is detected by a further planning scan.

The geometry of the immobilization device may change marginally if the patient is located therein (e.g., the immobilization device may expand). In one embodiment, to account for such minimal changes in the therapy planning, a common planning data record is created with recordings of the body region to be treated, and the filter and the therapy plan are created on the basis of the common planning data record. A shared data record, which is obtained by a single planning scan of the patient, the immobilization device and the filter, is also useful if it is already known from a diagnosis data record, for example, that a filter is needed for the irradiation.

In one embodiment, a filter apparatus for a particle therapy system includes a filter for adjusting the depth of penetration of the particle beam and an immobilization device for immobilizing a body region of a patient to be treated. The filter includes a deformable filter mass, which, by adjusting the geometry of the deformable filter mass to the geometry of the immobilization device, is applied to the immobilization device.

The advantages and embodiments listed above with respect to the method also apply to the filter apparatus.

In one embodiment, the filter mass is a gelatin mass. The gelatin mass can be easily produced and is food safe, so that the gelatin mass be used near the patient. The quantity needed to form the filter may also be cut to size easily.

In one embodiment, a cover, as described above, is attached to the surface of the filter mass to fix the filter mass.

DETAILED DESCRIPTION OF THE DRAWINGS

Figure 1:
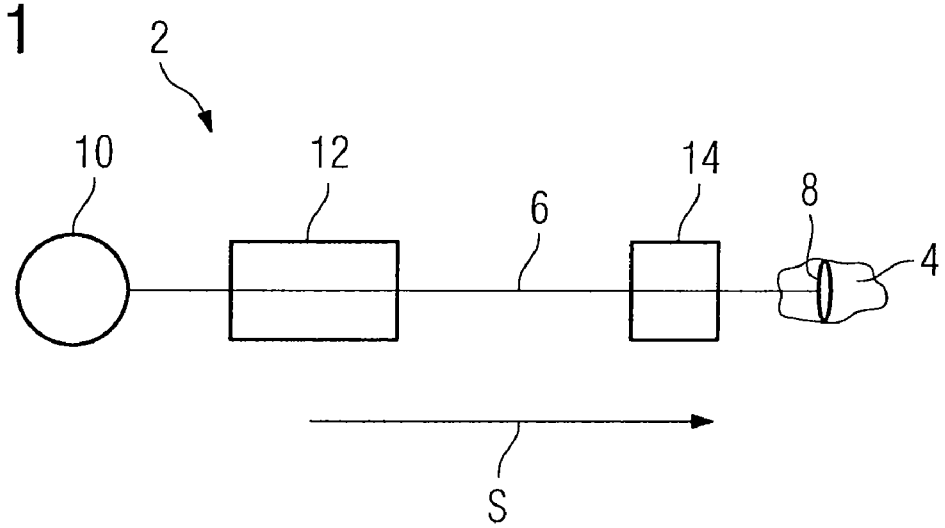
FIG. 1 shows a simplified particle therapy system.

FIG. 1 shows a basic diagram of a particle therapy system 2. The particle therapy system 2 is used to irradiate a body region 4 to be treated (e.g., a tumor tissue 4 of a patient (not shown)) with the aid of a particle beam 6. A disk-type section 8 of the tumor 4 (e.g., a layer 8) is treated in each step.

The particle beam 6 is generated in an accelerator 10, which is controlled by a control unit 12. The accelerator 10 supplies the particle with energy for the current layer 8 to be irradiated. The control unit 12 includes a grid scan apparatus (not shown here), which deflects the beam 6 both in the horizontal and the vertical directions, in order to scan the tumor tissue 4 within the layer 8. In one embodiment, the grid scan apparatus includes two pairs of magnets to deflect the beam 6.

Figure 2:
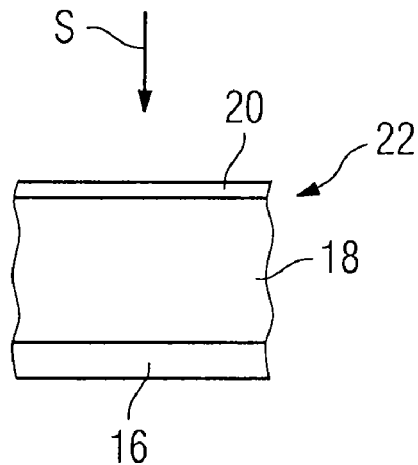
FIG. 2 shows one embodiment of a filter apparatus.

If the tumor 4 is located at least partially at a depth less than 20 mm below the skin surface, the energy of the accelerator 10 may not be adjusted such that the particles penetrate the patient at a lower depth. In this case, a filter apparatus 14, which is positioned between an exit window of the particle therapy system and the patient, is used for the passive adjustment of the energy of the particles. Such a filter apparatus 22, which is arranged in direct proximity to the patient (e.g., on the patient) is shown in FIG. 2. The filter apparatus 22 includes an immobilization device 16, which is directly connected to the patient. If the tumor 4 is in the head region, for example, the immobilization device 16 is an immobilization mask made of a thermoplastic material, which is adjusted to the face contours of the patient.

A layer of deformable filter mass 18 (e.g., a gelatin mass) is applied to the immobilization device 16, so that the particles are decelerated upon impact with the gelatin atoms. The depth of penetration of the particle beam 6 may thus be reduced using the gelatin mass.

A cover 20 (e.g., fashioned according to a type of plastic fixing layer) is provided on the surface of the gelatin mass 18, the fixing layer retaining the soft, deformable gelatin mass 18. In one embodiment, the filter mass 18 may be rigid, and a cover 20 is not used. The deformable filter mass 18 and the cover 20 form a filter 22 for adjusting the depth of penetration of the particle beam 6. The filter 22 may cover the complete immobilization device 16, or the filter 22 may be applied to a sub-region of the immobilization device 16.

Prior to the treatment, the filter apparatus 14 is created during a planning scan (e.g., using a CT device (not shown in more detail here)) so that the thickness and the homogeneity of the gelatin mass 18 are determined and accounted for during the therapy planning. In the planning scan, recordings of the tumor 4 may be obtained, and the immobilization device 16 and the filter 22 are also detected.

In one embodiment, in a first planning act, the filter apparatus 14 is not placed on the patient and a first planning data record is obtained by a first planning scan of the immobilized patient. The first planning scan contains information relating to the tumor 4 and the immobilization device 16. A second planning data record, which contains the recordings of the filter apparatus 14 (e.g., the immobilization device 16 and the filter 22), is obtained by a second planning scan after evaluating the first planning data record. During the evaluation of the second planning scan, the thickness distribution, quality and local homogeneity of the filter mass 18 are determined. A "Matching" combines the two planning data records and creates the therapy plan on this basis.

As a result of the properties of the filter 22 being determined before the treatment, the requirements in terms of geometry and homogeneity are not as high as in the case of a conventional filter plate made from PMMA, but the adjustment of the depth, which the particle beam 6 reaches in the patient body, is very precise.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for creating a therapy plan for a particle therapy, the method comprising:
adjusting the geometry of a deformable filter mass of a filter to the geometry of an immobilization device;
applying, at least partially, the deformable filter mass to the immobilization device;
obtaining a planning data record with a recording of the filter; and
determining properties of the filter to be used for the therapy plan using the planning data record,
wherein the filter is used to adjust the depth of penetration of a particle beam, and
wherein the immobilization device is used to immobilize a body region of a patient to be treated.

2. The method as claimed in claim 1, wherein determining properties of the filter comprises:
taking account of the thickness distribution, the homogeneity, or the thickness distribution and the homogeneity of the deformable filter mass.

3. The method as claimed in claim 1, wherein the immobilization device is an immobilization mask.

4. The method as claimed in claim 1, wherein a cover is applied to a surface of the deformable filter mass.

5. The method as claimed in claim 1, further comprising:
obtaining a first planning data record with recordings of the body region to be treated, which is immobilized using the immobilization device;
obtaining a second planning data record with recordings of the immobilization device with the filter; and
balancing the first planning data record with the second planning data record in order to optimize the therapy plan.

6. The method as claimed in claim 1, wherein the planning data record is a shared planning data record that is obtained with recordings of the body region to be treated with the attached immobilization device and the filter.

7. A filter apparatus for a particle therapy system, the filter apparatus comprising:
a filter for adjusting the depth of penetration of a particle beam; and
an immobilization device for immobilizing a body region of a patient to be treated,
wherein the filter comprises a deformable filter mass that is applied to the immobilization device by adjusting the geometry of the deformable filter mass to the geometry of the immobilization device.

8. The filter apparatus as claimed in claim 7, wherein the deformable filter mass is a gelatin mass.

9. The filter apparatus as claimed in claim 7, wherein a cover is applied to a surface of the deformable filter mass.

10. The filter apparatus as claimed in claim 8, wherein a cover is applied to a surface of the deformable filter mass.

11. The method as claimed in claim 2, wherein the immobilization device is an immobilization mask.

12. The method as claimed in claim 2, wherein a cover is applied to a surface of the deformable filter mass.

13. The method as claimed in claim 3, wherein a cover is applied to a surface of the deformable filter mass.

14. The method as claimed in claim 2, further comprising:
obtaining a first planning data record with recordings of the body region to be treated, which is immobilized using the immobilization device;
obtaining a second planning data record with recordings of the immobilization device with the filter; and
balancing the first planning data record with the second planning data record in order to optimize the therapy plan.

15. The method as claimed in claim 3, further comprising:
obtaining a first planning data record with recordings of the body region to be treated, which is immobilized using the immobilization device;
obtaining a second planning data record with recordings of the immobilization device with the filter; and
balancing the first planning data record with the second planning data record in order to optimize the therapy plan.

16. The method as claimed in claim 4, further comprising:
obtaining a first planning data record with recordings of the body region to be treated, which is immobilized using the immobilization device;
obtaining a second planning data record with recordings of the immobilization device with the filter; and balancing the first planning data record with the second planning data record in order to optimize the therapy plan.

17. The method as claimed in claim 2, wherein the planning data record is a shared planning data record that is obtained with recordings of the body region to be treated with the attached immobilization device and the filter.

18. The method as claimed in claim 3, wherein the planning data record is a shared planning data record that is obtained with recordings of the body region to be treated with the attached immobilization device and the filter.

19. The method as claimed in claim 4, wherein the planning data record is a shared planning data record that is obtained with recordings of the body region to be treated with the attached immobilization device and the filter.

* * * * *